(12) United States Patent
Watanabe et al.

(10) Patent No.: US 6,876,198 B2
(45) Date of Patent: Apr. 5, 2005

(54) MAGNETIC RESONANCE IMAGING SYSTEM

(75) Inventors: Shigeru Watanabe, Ibaraki (JP); Tetsuhiko Takahashi, Saitama (JP); Hirotaka Takeshima, Ibaraki (JP); Hiromichi Shimizu, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 15 days.

(21) Appl. No.: 10/380,115

(22) PCT Filed: Sep. 11, 2001

(86) PCT No.: PCT/JP01/07870

§ 371 (c)(1),
(2), (4) Date: Mar. 11, 2003

(87) PCT Pub. No.: WO02/22012

PCT Pub. Date: Mar. 21, 2002

(65) Prior Publication Data

US 2004/0039277 A1 Feb. 26, 2004

(30) Foreign Application Priority Data

Sep. 11, 2000 (JP) .................................... 2000-274832

(51) Int. Cl.[7] ............................................. G01V 3/00
(52) U.S. Cl. ................................... 324/309; 324/307
(58) Field of Search ............................. 324/309, 307, 324/306, 312, 314, 300; 600/410, 411, 422, 423

(56) References Cited

U.S. PATENT DOCUMENTS

| | | | | |
|---|---|---|---|---|
| 5,708,359 A | * | 1/1998 | Gregory et al. | 324/309 |
| 6,289,233 B1 | * | 9/2001 | Dumoulin et al. | 600/410 |
| 6,400,157 B1 | * | 6/2002 | Bonanni et al. | 324/322 |
| 6,680,610 B1 | * | 1/2004 | Kyriakos et al. | 324/307 |

* cited by examiner

*Primary Examiner*—Louis Arana
(74) *Attorney, Agent, or Firm*—Antonelli, Terry, Stout & Kraus, LLP (57) ABSTRACT

A magnetic resonance imaging apparatus is provided with a sequencer for executing a rapid imaging sequence of up to 100 ms at a full scan, a parallel measurement system for executing a partial encoding measurement in which the number of phase encoding operations performed for the measurement is reduced, an image processing system for reconstructing images from the information obtained though parallel measurements and composing reconstructed images of a plurality of areas to make one image, a display system for displaying the obtained images at a rate of 50 frame/second or more, and an image renewal system for taking in coordinate information of the cross-section to be imaged from position and pointing devices at intervals of about 0.1 second, and renewing the cross-section to be imaged in real time. Thus, imaging on the cross-sections indicated by a device can be performed in real time with high spatial and high time resolution.

15 Claims, 9 Drawing Sheets

MAGNETIC RESONANCE IMAGING SYSTEM

In this magnetic resonance imaging apparatus, the reception system has a receiving coil, which is composed of a plurality of overlapped coils, and the receiving coil detects plural series of echo signals. The signal processing system divides these echo signals into plural regions, performs an image reconstruction operation in parallel using the plural series of echo signals, and combines images of the plural regions into one image. The sequencer executes an ultra-rapid imaging sequence, and, at the same time, it reduces the number of phase encoding operations used in the measurement. This sequencer further includes image renewal means for renewing the cross-section to be imaged in response to positional information corresponding to a desired angle and direction.

Further, this magnetic resonance imaging apparatus includes a insertion device which is inserted into the interior of the object to be examined, and the image renewal means renews the cross-section corresponding to positional information provided by the insertion device.

Further, in this magnetic resonance imaging apparatus, the image renewal means renews the cross-section corresponding to the positional information provided by the signals from a three-dimensional mouse.

Further, in this magnetic resonance imaging apparatus, the insertion device is provided with plural markers, and the image renewal means renews the cross-section corresponding to the positional information, which is a signal acquired on the basis of information received from plural cameras that are provided for detecting the movement of these markers.

Further, in this magnetic resonance imaging apparatus, the magnetic circuit is formed of magnets placed above and below the object to be examined and has two or less supporting means for supporting these magnets.

Further, in this magnetic resonance imaging apparatus, the sequencer performs a measurement in which the number of phase encoding operations used in the measurement is reduced in correspondence with the plural number of coils of said reception system.

Further, in this magnetic resonance imaging apparatus, the control means performs imaging processing for plural cross-sections to be imaged during one period of imaging processing and image reconstructing processing for plural cross-sections during one period of image reconstruction processing, and it displays a plurality of sections during one period of display processing.

Further, in this magnetic resonance imaging apparatus, the control means determines the first cross-section to be imaged, corresponding to the positional information received from the image renewal means, and determines other cross-sections that are parallel to the first cross-section.

Alternately, in this magnetic resonance imaging apparatus, the control means determines the first cross-section to be imaged corresponding to the positional information received from the image renewal means, and it determines another cross-section which is perpendicular to the first imaged cross-section.

BRIEF DESCRIPTION OF THE DRAWINGS

FIGS. 3A and 3B shows examples of static magnetic field generating magnets, wherein

FIGS. 4A and 4B show sequences employed in accordance with the present invention, wherein

FIGS. 8A and 8B illustrate several types of partial encoding, wherein

FIGS. 9A and 9B show an example of parallel MR imaging, wherein

BEST MODE FOR CARRYING OUT THE INVENTION

Hereinafter, an embodiment of the present invention will be described with reference to the drawings.

First, the overall structure of a magnetic resonance imaging apparatus to which the present invention is applied, will be described with reference to FIG. 2. This magnetic resonance imaging apparatus is designed to obtain a tomogram of an object to be examined, utilizing the NMR phenomenon. This apparatus is constituted of a static magnetic field generating magnetic circuit 2, a magnetic field gradient generating system 3, a transmission system 4, a reception system 5, a signal processing system 6, a sequencer 7, and a central processing unit (CPU) 8.

Figure 3A:
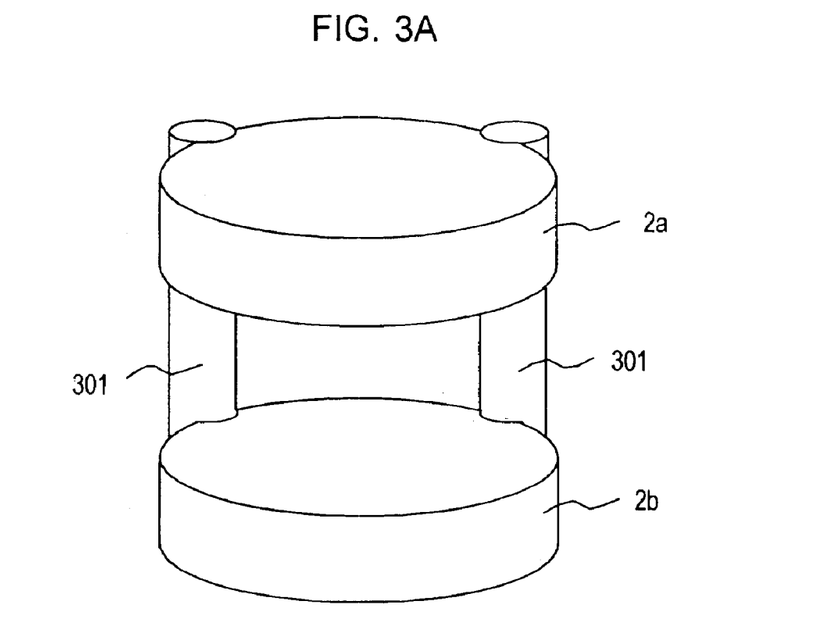
FIG. 3A is a diagram showing static magnetic field generating magnets having two supporting means.
Figure 3B:
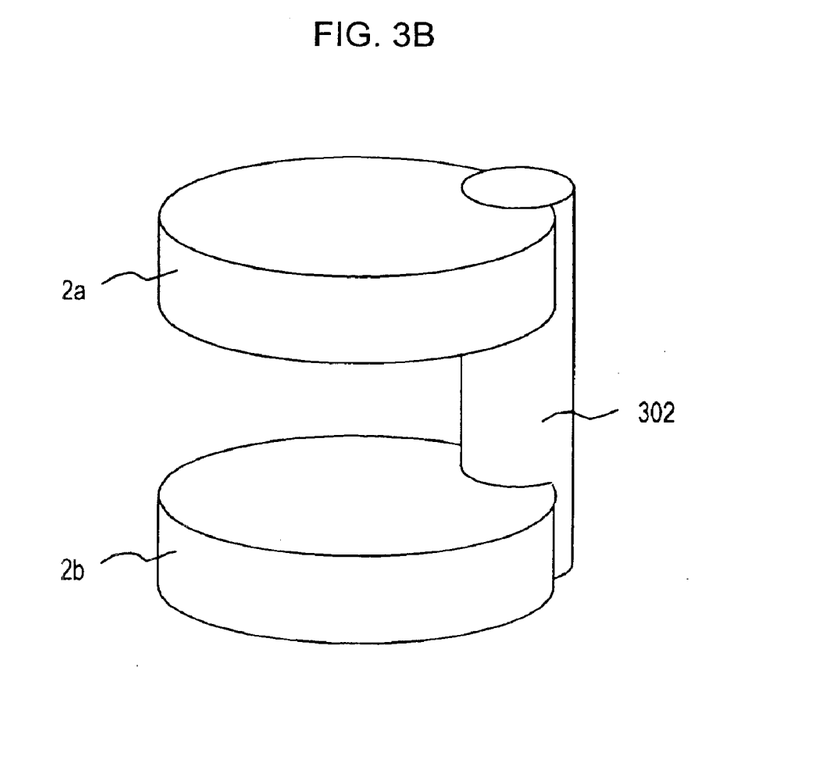
FIG. 3B is a diagram showing static magnetic field generating magnets having one supporting means.

In the static magnetic field generating magnetic circuit 2, which is designed to generate a uniform static magnetic field around an object 1 to be examined. magnetic field generating means of the permanent magnet type, resistive magnet type, or superconductive magnet type is placed within a space which is expanded to some extent. This static magnetic field generating magnet employs an open structure, in which a wide opening is provided, so that an operator can easily access the object. In this open structure, access to the object becomes easy when supporting means 301 for supporting the upper and lower static magnetic field generating magnets 2a and 2b is, for example, constructed with two columns, which are asymmetrically located, as shown in FIG. 3A. Further, when supporting means 302 is constructed with one column, as shown in FIG. 3B, the openness and the accessibility to the object are further improved, and the object does not feel closed in. The form of the supporting means 301 and 302 in FIGS. 3A and 3B is a column, but it may also be a prism or other form, in consideration of the operation's accessibility or other factors. Similarly, any form may be employed for the static magnetic field generating magnets 2a and 2b, as long as these magnets are disposed in the space above and below the object to be examined, opposing each other. Incidentally, since it is necessary to shield against magnetic field leakage when superconductive coils are used in the static magnetic field generating magnetic circuit 2, a passive shield in which a ferromagnetic material, such as iron, is placed around the static magnetic field generating magnetic circuit 2; or, an active shield, in which a shield coil is placed outside the superconductive coils, is provided for said static magnetic field generating magnetic circuit 2, although this is not shown in the figure. In order to improve the uniformity of the static magnetic field, various kinds of members, such as a pole piece, shim material, and a shimming coil are provided, regardless of the use of a permanent magnet or a superconductive magnet, in consideration of the circumstances.

The magnetic field gradient generating system 3 is constituted of gradient field coils 9 wound in the directions of X-, Y-, and Z-axes, and a gradient magnetic field power supply 10 for driving these gradient magnetic field coils. In this magnetic field gradient generating system 3, the gradient magnetic fields Gx, Gy and Gz are applied to the object 1 by driving the gradient magnetic field power supply 10 for the gradient magnetic field coils on the X-, Y-, and Z-axes in accordance with signals received from the sequencer 7, which will be described later. The slice plane of the object can be determined by the manner of application of the gradient magnetic fields to the object 1.

The sequencer 7 repeatedly applies a radio-frequency magnetic field pulse for generating nuclear magnetic resonance in atomic nuclei constituting the anatomy of the object 1, in accordance with a predetermined pulse sequence. This sequencer 7 is operated under control of the CPU 8 and is programmed to send various kinds of commands necessary for acquisition of data for the tomogram to the transmission system 4, the magnetic field gradient generating system 3, and the reception system 5.

The transmission system 4 is designed to irradiate a radio-frequency magnetic field so as to generate nuclear magnetic resonance in atomic nuclei constituting the anatomy of the object 1 in accordance with a radio-frequency pulse transmitted from the sequencer 7. This system is constituted of a radio-frequency oscillator 11, a modulator 12, a radio-frequency amplifier 13, and a radio-frequency coil 14a for transmission. In the transmission system 4, a radio-frequency pulse output by the radio-frequency oscillator 11 is amplitude-modulated by the modulator 12 according to the control provided by the sequencer 7. This amplitude-modulated radio-frequency pulse is amplified by the radio-frequency amplifier 13, and the pulse is then supplied to the radio frequency coil 14a, which is located near the object 1. In this manner, electromagnetic waves are irradiated to the object 1.

The reception system 5 is designed to detect the echo signals that are generated due to nuclear magnetic resonance in the atomic nuclei of the anatomy of the object 1, and it is constituted of a multi-channel radio-frequency coil (multi-array coil) 14b, in which a plurality of radio-frequency coils are overlapped, an amplifier group 15, a quadrature phase detector 16, and an A/D converter 17. In this reception system 5, the electromagnetic waves (the NMR signals), which are generated from the object 1 In response to the electromagnetic waves irradiated from the radio-frequency coil 14a for transmission, are detected at the multi-channel radio-frequency coil 14b, which is positioned close to the object 1, and the detected signals are input to the A/D converter 17 via the amplifier group 15 and the quadrature phase detector 16, so as to convert the signals into a digital quantity. Further, these signals are formed into two series of data sampled by the quadrature phase detector 16 in accordance with the timing commanded by the sequencer 7, and they are sent to the signal processing system 6.

The signal processing system 6 is constituted of a CPU 8, a recording device, such as a magnetic disk 18 and a magneto-optical disk 19, and a display 20, such as a CRT. In the CPU 8, processing, such as Fourier transformation, correction and the like, is performed on the respective channels of the multi-array coil, so as to produce images of signal strength distributions in the regions allocated to the respective channels. These images are combined and displayed on the display 20 as a tomogram of any cross-section.

Figure 2:
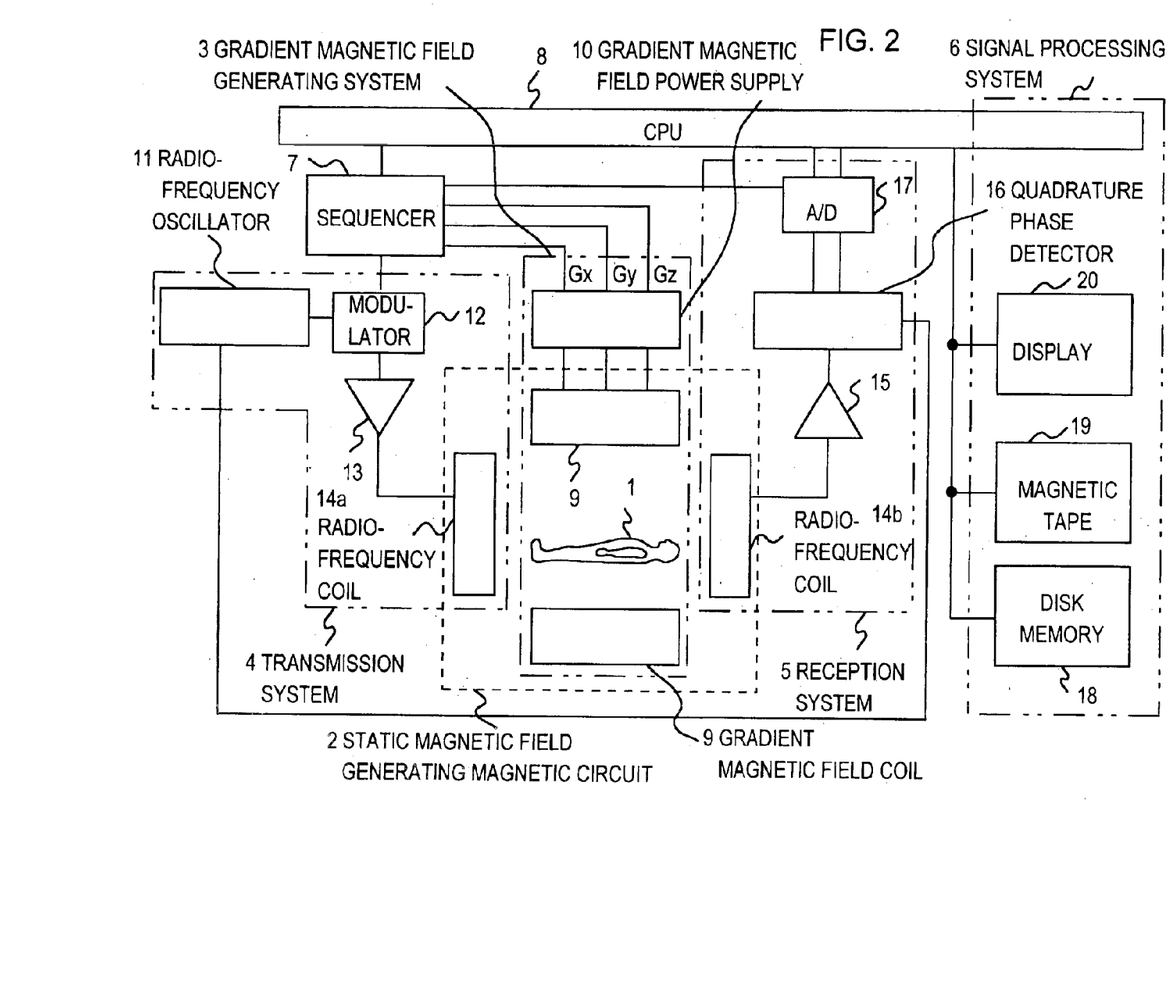
FIG. 2 is a block diagram showing the overall structure of an MRI apparatus according to the present invention.

Incidentally, in FIG. 2, the radio-frequency coils 14a and 14b for transmission and reception, respectively, and the gradient magnetic field coil 9 are placed within the space of the magnetic field generated by the static magnetic field generating magnetic circuit 2 around the object 1.

Next, various means for improving the real-time performance of a magnetic resonance imaging apparatus will be described individually.

Figure 4A:
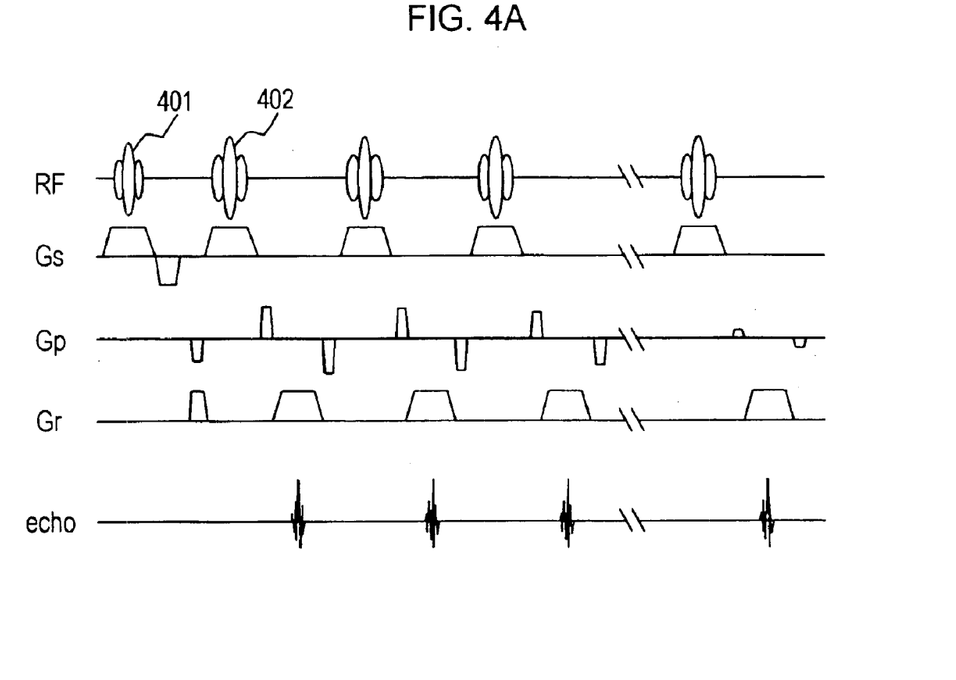
FIG. 4A is a timing chart showing the pulse sequence of a fast sign echo (FSE)
Figure 4B:
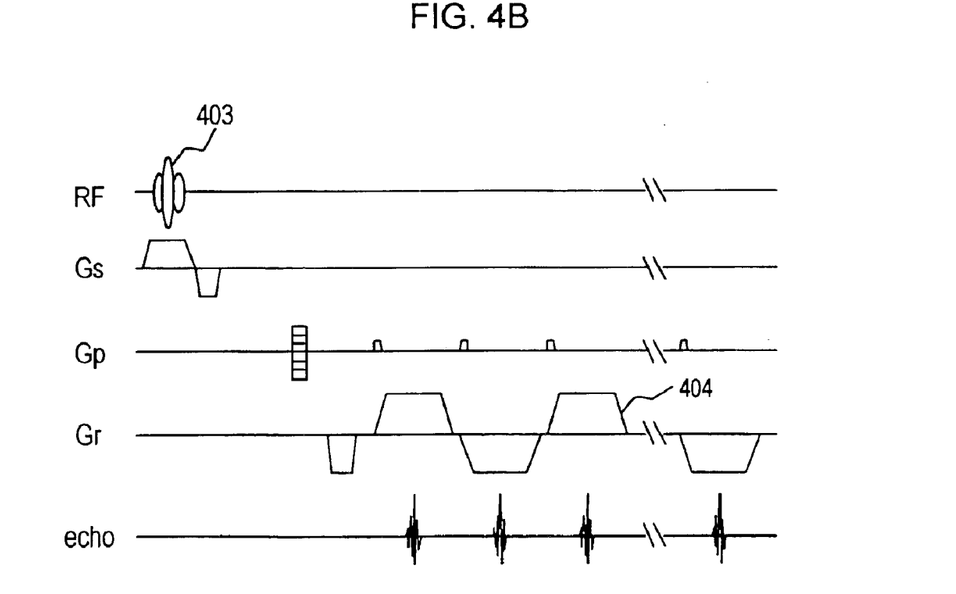
FIG. 4B is a timing chart showing a pulse sequence of an echo planer imaging (EPI).

The imaging sequence that is used may be a spin echo method of a gradient echo method, which are basic imaging sequences, as well as the echo planer (hereinafter referred to as EPI) method or the fast spin echo (hereinafter referred to as FSE) method, which are fast imaging sequences. As shown in FIG. 4A, the FSE sequence is a practicable fast sequence for obtaining an image quality close to that obtained by the conventional SE sequence. This FSE sequence is realized by dividing a RARE sequence into plural sequences, the RARE sequence being designed to obtain one image at high speed by applying a different quantity of the phase encoding gradient magnetic fields to each echo signal, an application of the multi-echo method in which multiple echoes are generated by repeatedly applying an inversion pulse 402 to the transverse magnetization generated by the excitation of a 90° pulse 401. On the other hand, as shown in FIG. 4B, the EPI sequence is a method of acquiring plural echoes with one excitation pulse 403 by rapidly alternating the polarity of a readout gradient magnetic field 404, without inversion by a RF pulse. Although a rapid imaging of several tens ms can be performed with this EPI sequence, it is extremely sensitive to the nonuniformity of the static magnetic field. In accordance with the present invention, such fast sequences as the above-described FSE sequence and EPI sequences may effectively be used.

Figure 5:
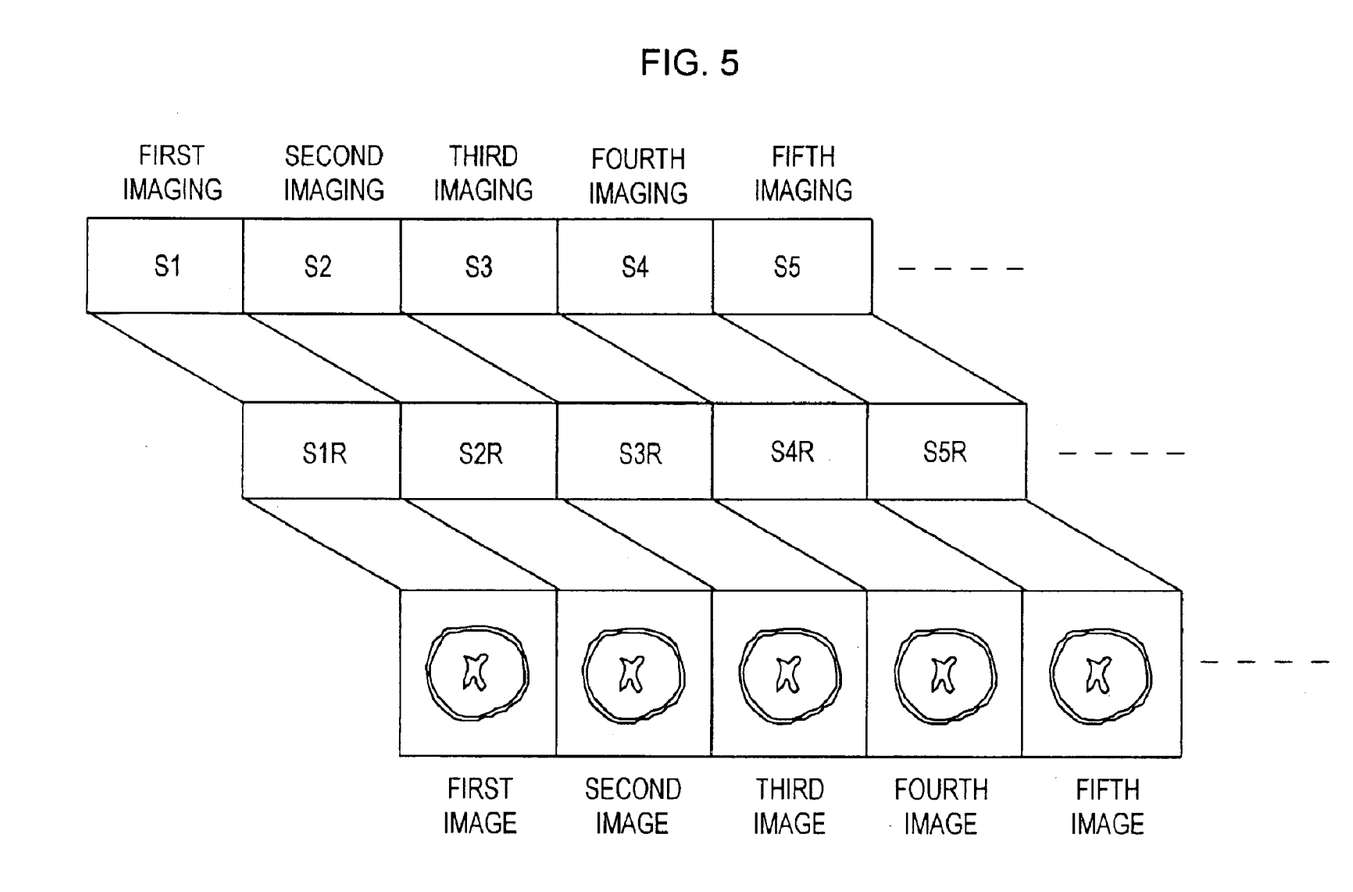
FIG. 5 is a diagram illustrating an example of fluoroscopy.

In accordance with the present invention, this kind of fast sequence is applied to realize fluoroscopy, which is a real-time dynamic imaging method. In fluoroscopy, a short-time imaging performance within a second and real-time image reconstruction are repeatedly performed; and, thus, visualization of the dynamics of tissue in a body, as in fluoroscopy using x-rays, and a grasp of the position of a device inserted into the interior of a body of the object from the outside are enabled. The fluoroscopy is described with reference to FIG. 5. In the fluoroscopy, imaging is continuously performed on a predetermined slice, image reconstruction is performed after each imaging, and the images which have been reconstructed are displayed. Thus, continuous images, that is, moving images, can be obtained.

Fluoroscopy has been increasingly applied to achieve minimally invasive imaging during surgery, which is generally referred to as interventional MRI (hereinafter referred to as IVMR). The fluoroscopy in IVMR is likely to be used as imaging means for guiding a biopsy needle or a catheter (hereinafter referred to as a "device") to a lesion. Further, after the device reaches the lesion, the therapy can be monitored by creating images of physical or chemical change in the treated tissue in the process of the therapy.

Figure 6A:
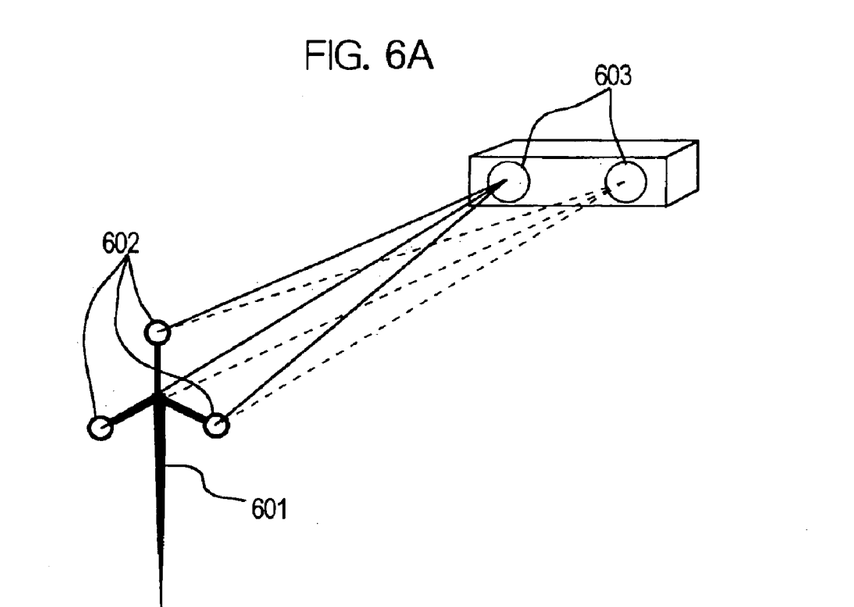
FIGS. 6A and 6B are diagrams illustrating interactive scanning.
Figure 6B:
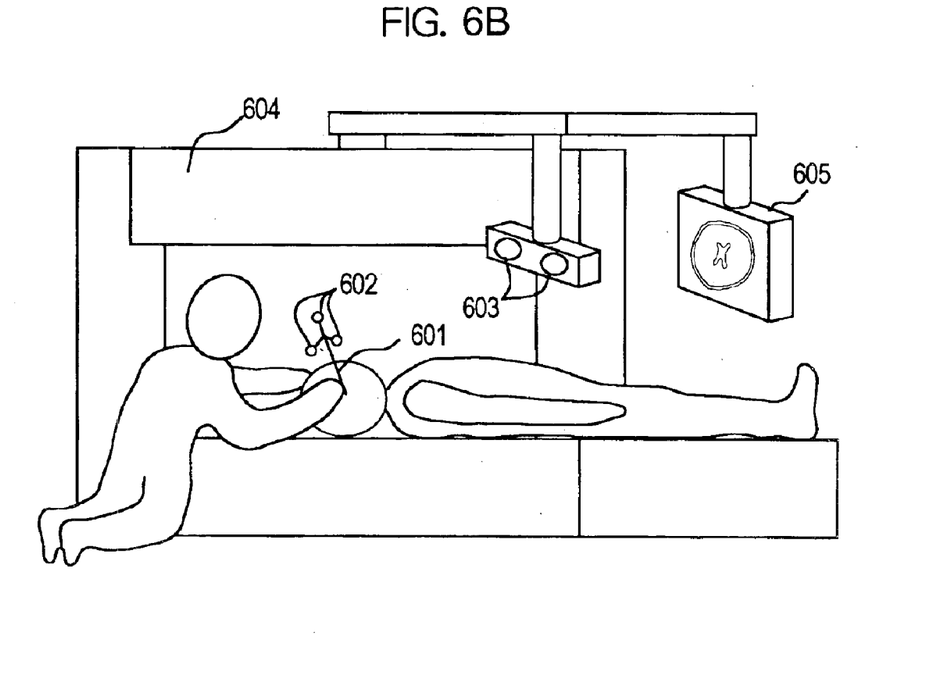
Figure 7:
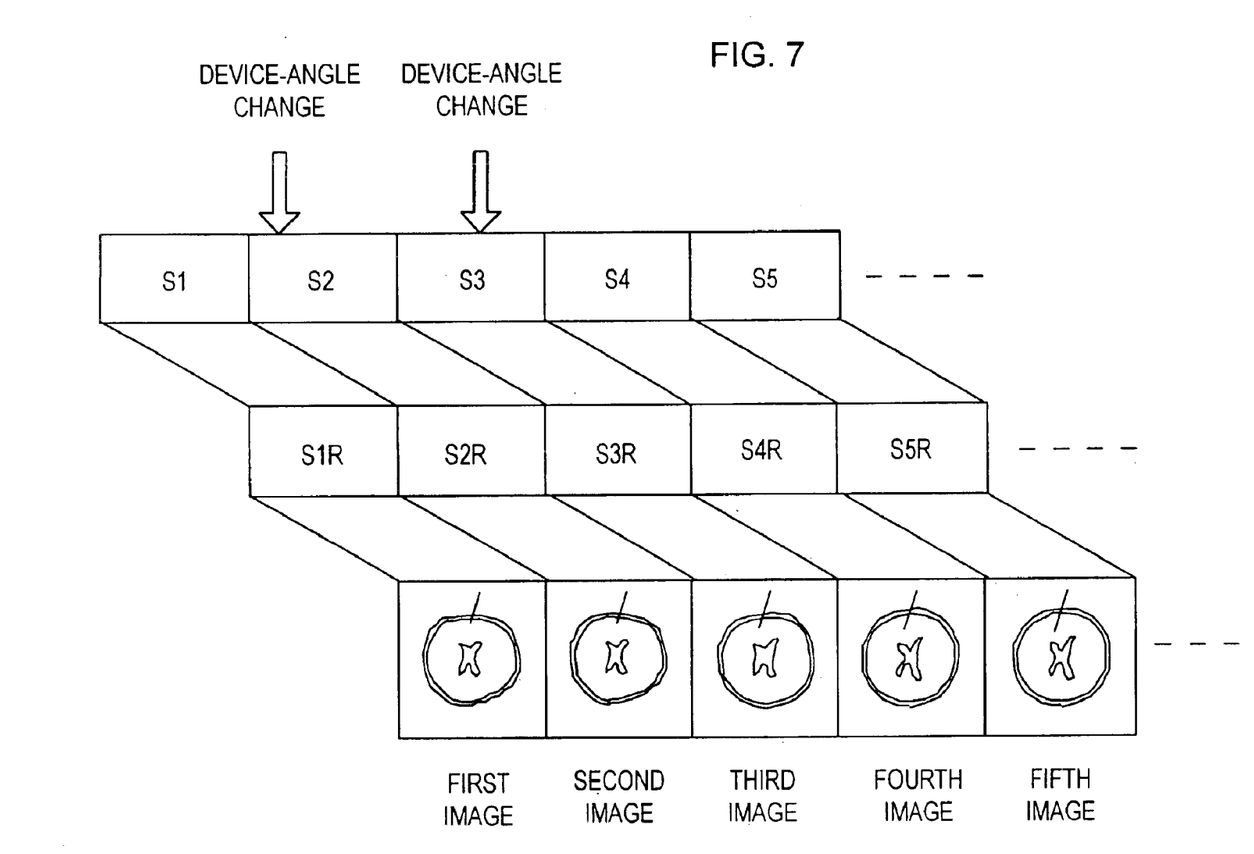
FIG. 7 is a diagram illustrating an example of fluoroscopy, in which the interactive scanning is employed.

When fluoroscopy is used for the monitoring of therapy and the imaging plane in this fluoroscopy is fixed, it may not be possible to image the tip of a biopsy needle or the like if the device moves out of the imaging plane due to movement of the patient. To solve this problem, a method referred to as interactive scanning, which is shown in FIGS. 6A and 6B, is employed. Interactive scanning is a method in which a device 601, such as a biopsy needle, is provided with three markers 602 for indicating the position of the device in three-axis directions. The markers 602 are viewed by two cameras 603, and the position and the inclination of the device 601 is thus detected. As shown in FIG. 6B, the cameras 603 and a monitor 605 are mounted on the magnetic resonance imaging apparatus 604, and the markers 602 are provided on the device 601, which is manipulated by an operator. In an apparatus having this structure, the imaging plane is set to correspond to the orientation of the device 601. The device is then moved by the surgeon, and the cameras 603 view the movement of the markers 602, so that the position and inclination of the device 601 can be detected. The imaging plane is reset accordingly, and, thus, a new image for the imaging plane is displayed on the monitor 605 at all times. That is, as shown in FIG. 7, the image of a cross-section in the direction of the device can be constantly obtained in real time. In this manner, by performing interactive scanning in the fluoroscopy. Imaging can be performed with a higher time resolution, and the response speed in the tracking of the device can be improved. Thus, the guiding of the device can be completed within a short time. Further, by performing multi-slice imaging jointly with this fluoroscopy, successive images of plural tomograms can be obtained. These tomograms may be those of planes parallel to the cross-section in the direction of the device, or they may be perpendicular thereto.

Next, another problem will be considered. That is, the time resolution can be improved simply by shortening the repetition time (TR) and reducing the number of phase encoding operations so as to shorten the imaging time for one image; however, in this case, the S/N ratio is lowered and the spatial resolution is deteriorated, with the result that the image quality is deteriorated. To solve this problem, a method referred to as partial phase encoding (partial encoding) is used, in which the time resolution is improved by reusing a part of the measurement data obtained during the imaging, as shown in FIG. 7.

Figure 8A:
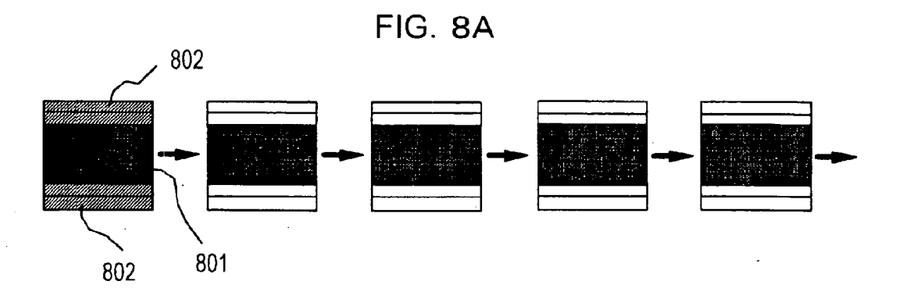
FIG. 8A is a diagram illustrating Keyhole imaging.
Figure 8B:
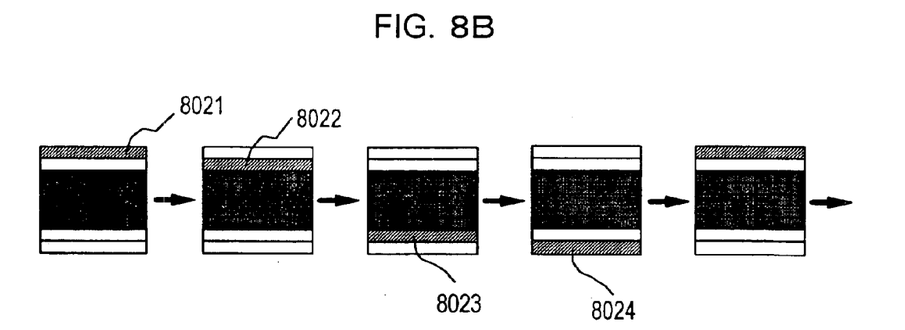
FIG. 8B is a digram illustrating Keyhole imaging, in which the outside region of the k space is sequentially renewed.
Figure 8C:
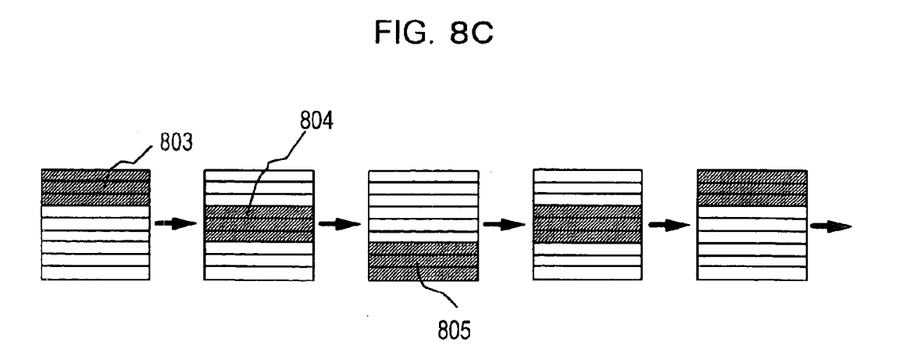
FIG. 8C is a diagram illustrating partial encoding, in which the outside region and the center region of the k space are alternately measured.

As a typical example of partial encoding, a keyhole measurement as shown in FIG. 8A is used. The keyhole measurement is designed to improve the time resolution when the tissue to be examined does not move and only its signal strength changes. This keyhole measurement utilizes the characteristic that contrast information is predominantly determined by the data of the central portion 801 of the k space. However, if it is applied to moving tissue, artifacts occur, since the data of outer portions of the k space (spatial high-frequency information) is not renewed. In this case, a method is employed in which portions 8021–8024 of the k space are sequentially renewed, as shown in FIG. 8B. As another example, a method is also employed in which the data of the outer portions 803 and 805 and the data of the central portion 804 are alternately measured, as shown in FIG. 8C. By any of the above-described methods, the time resolution can be improved, and these methods may be creatively used according to various circumstances. Incidentally, a detailed description of the keyhole measurement is set forth in Brummer, et al. "Composite k-space windows (Keyhole Techniques) to improve temporal resolution in A dynamic series of images following contrast administration," SMRM Proc., P4236, 1996. Also, the details of another partial encoding measurement method are described by Mistlletta et al. (U.S. Pat. No. 5,713,358 and U.S. Pat. No. 5,830,143).

Figure 9A:
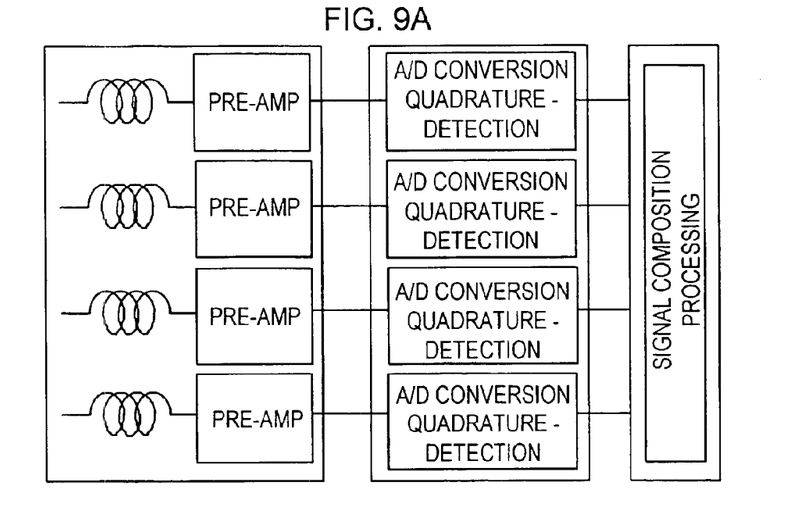
FIG. 9A is a diagram showing the composition of multi-coil array used in parallel MRI.
Figure 9B:
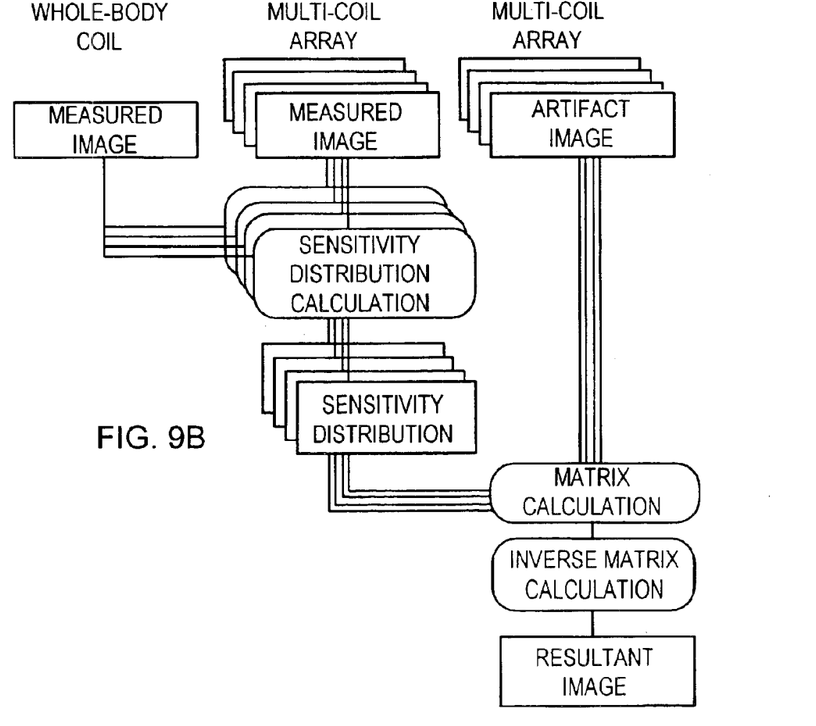
FIG. 9B is a flow chart illustrating the parallel MRI.

To shorten the imaging time, a method referred to as a parallel MRI is used. Parallel MRI is a method in which imaging is performed after selectively eliminating data in the phase-encoding direction, using a multi-array coil, which is constructed by overlapping plural coils. More specifically, in this method, a multi-coil array consisting of plural coils that are arranged as shown in FIG. 9A is used. As shown in FIG. 9B, imaging is performed after selectively thinning out the phase encoding operations at each coil to a predetermined number (the same as the number of coils, usually). Then, according to the sensitivity distribution obtained in advance by the coils for the whole body, or each individual coil, artifacts generated on each image are eliminated by using a matrix operation, and an image is thus obtained. Since the number of phase encoding operations is thinned out in this manner, the imaging time can be shortened.

In the above-described method, means for performing imaging at high speed and means for freely changing the cross-section for imaging are improved. However, both of these means are not optimized in this system, and the functions of these means have not been systematically united to each other. On the other hand, the present invention has achieved optimization and a uniting of the functions of these means by constituting an apparatus as described below. That is, the sequencer executes a rapid imaging sequence (100 ms or less in full scan), and the measurement system performs a partial encoding measurement in which the number of phase encoding operations in the measurement is reduced; and, it also performs parallel MRI in which the data obtained at the multi-channel reception system (the multiple coil) is reconstructed into images, and the reconstructed images of the plural regions are combined into one image. Further, the image processing system takes in coordinate information relevant to the cross-section to be imaged from the device at such intervals that the information can be recognized in real time (at intervals of about 0.1 second), whereby the cross-section is renewed in real time. Thus, the display system can display a series of the obtained images at high speed (at a rate of 50 frames/second or more).

Figure 1:
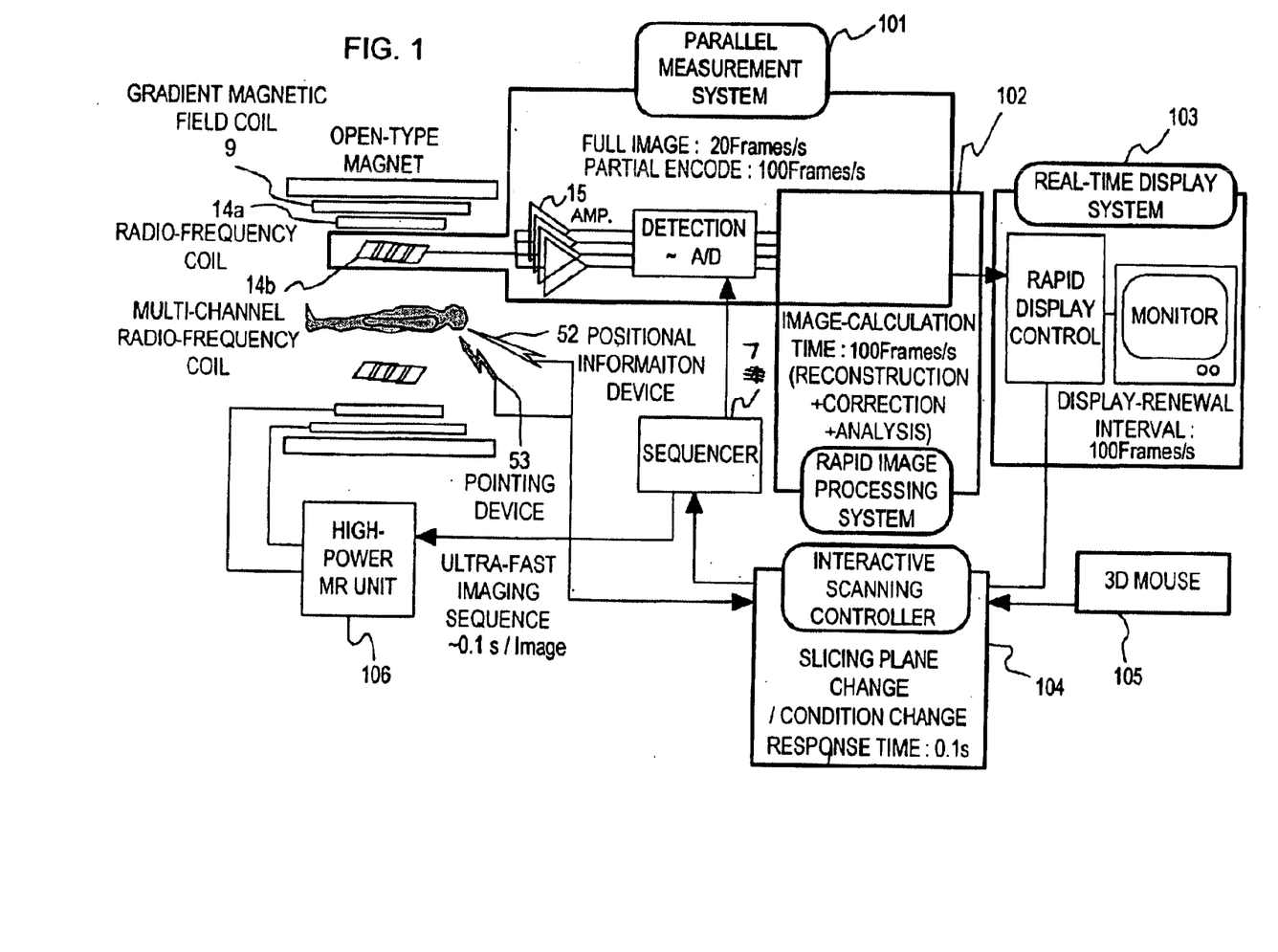
FIG. 1 is a functional block diagram of an interactive MRI system, which represents an embodiment of the present invention.

The functional structure of the apparatus according to the embodiment of the present invention is shown in FIG. 1. That is, the magnetic resonance imaging apparatus according to the present invention is constituted of:

(1) a sequencer 7 for executing a fast imaging sequence, such as an EPI and a FSE;

(2) a parallel measurement system 101 that is capable of executing rapid imaging (100 images/s, for example) by using partial encoding measurement, wherein the application of phase encoding is reduced, and by obtaining data for one image by receiving echo signals in parallel using the multi-channels of the multi-coil array 14b; performing A/D conversion through use of the amplifier group 15 on the plural series of the echo signals being detected; performing an image reconstruction operation in parallel on the echo signals that are divided into plural regions; and combining images of the plural regions;

(3) a rapid imaging processing system 102 for executing image reconstruction at high speed on the image data obtained in the above-described rapid imaging;

(4) a real-time display system 103 for displaying the obtained images at a high frame rate (100 frame/second, for example);

(5) an interactive scanning control 104 for taking in the coordinate information of the cross-section to be imaged from a device for IVMR (a positional information device 52, a pointing device 53 provided on a biopsy needle, or the like) at such intervals that the surgeon can check information in real time, and for renewing the cross-section in real time; and (6) a high-power MR unit 106 for supporting enough electric power to gradient magnetic field coils 9 and transmission coils 14*a* for a rapid imaging sequence to be executed.

With the above-described construction, the present invention can provide a real-time MR system capable of performing fluoroscopy with high time resolution and good response to any operation carried out by the operator.

When it is assumed that a desired cross-section will be selected by the operator during fluoroscopy, the apparatus may further include:

(7) A 3D mouse 105 with which cross-sectional information can be input freely by the operator.

In the magnetic resonance imaging apparatus constructed in the above-described manner, a topographic plane, including the biopsy needle and the tissue being examined, can be set according to information of the positional information device 52 provided on the needle, or the pointing device 53 by which the positional information can be freely input. This positional information can be renewed in real time, for instance, each 0.1 second, and the tomographic plane including the needle can thereby be traced at any time, even when the patient moves as the needle proceeds. Further, since a partial encoding and a space-dividing measurement (a parallel measurement) are used at the same time, the number of phase encoding operations performed in every measurement can be reduced to $\frac{1}{10}$, and new images can be thus made every 10 ms. Further, by employing a real-time display system, image renewal with a high time resolution can be performed. Thus, such devices as a biopsy needle and the like can be smoothly guided to a lesion.

Since the apparatus according to the present invention is constructed in the above-described manner, a tomographic plane, including the direction of the needle's movement, can be automatically determined as the operator handles the biopsy needle, and the cross-section can be traced even when the patient moves. Further, since the image is renewed with a high time resolution, changes inside the patient due to handling of the biopsy needle can be checked in real time. Also, since the apparatus is optimized in this system, information of the tomographic plane needed for efficient treatment can be obtained, and further, there is no need to increase the cost of the respective functions.

What is claimed is:

1. A magnetic resonance imaging apparatus for obtaining tomograms by repeatedly performing measurement of echo signals generated due to nuclear magnetic resonance, comprising:

a magnetic circuit for applying a static magnetic field to an object to be examined, which has an open structure;

gradient magnetic field generating means for applying a gradient magnetic field to the object;

a sequencer for repeatedly applying the gradient magnetic field and a radio-frequency magnetic field with a predetermined pulse sequence;

a transmission system for irradiating the radio-frequency magnetic field so as to generate nuclear magnetic resonance in atomic nuclei in a tissue of the object;

a reception system for detecting each signals generated due the nuclear magnetic resonance;

a signal processing system for making one image, using the echo signals detected by said reception system; and means for displaying the obtained image, wherein said reception system is constructed by overlapping plural coils and thus detects plural series of echo signals with a reduction of phase encoding operations;

said signal processing system performs an image reconstruction operation in parallel on the plural series of echo signals divided into plural regions, and combines images of the plural regions into one image;

said sequencer executes a rapid imaging sequence, and performs measurement by measuring data in one part of a k space and reusing the data measured in an other part of the k space, and the apparatus further comprises image renewal means for renewing the cross-section to be imaged according to positional information of any angle and direction.

2. A magnetic resonance imaging apparatus according to claim 1, wherein an insertion device which is inserted to the interior of the object is provided, and said image renewal means renews the cross-section to be image based on the positional information of a portion of said insertion device which is outside of the object.

3. A magnetic resonance imaging apparatus according to claim 2, wherein said image renewal means reviews the cross-section to be imaged based on the positional information being signals acquired based on information from plural cameras for tracking movement of plural markers provided on said insertion device.

4. A magnetic resonance imaging apparatus according to claim 1, wherein said image renewal means renews the cross-section to be imaged based on the positional information provided by the signal from a three-dimensional mouse.

5. A magnetic resonance imaging apparatus according to claim 1, wherein said magnetic circuit is constituted of magnets oppositely placed above and below the laid object, and supporting means for supporting the magnets, in which the number of this supporting means is two or less.

6. A magnetic resonance imaging apparatus according to claim 1, wherein said sequencer performs measurement with phase encoding operations whose number is reduced to the number of coils in said reception system.

7. A magnetic resonance imaging apparatus comprising:

a magnetic circuit for applying a static magnetic field to an object to be examined, which has an open structure;

gradient magnetic field generating means for applying a gradient magnetic field to the object;

a sequencer for applying the gradient magnetic field and a radio-frequency magnetic field with a predetermined pulse sequence;

a transmission system for irradiating a radio-frequency magnetic field so as to generate nuclear magnetic resonance to atomic nuclei in a tissue of the object;

a reception system for detecting echo signals generated due to the nuclear magnetic resonance;

a signal processing system for making one image, using the echo signals detected at said reception system;

means for displaying the obtained image; and control means for controlling said sequencer, and transmission system, said reception system, and said signal processing system, so as to sequentially execute imaging processing in which said pulse sequence is executed to acquire the echo signals a predetermined number of times, sequentially execute image reconstruction processing for image-reconstructing the echo signals acquired by the imaging processing, said execute display processing for displaying each image which is reconstructed above, wherein said reception system is constructed by overlapping plural coils and thus detects plural series of echo signals with a reduction of phase encoding operations, said signal processing system performs the image reconstruction operations in parallel after dividing said plural series of echo signals into plural regions, and then combines images of the plural regions into one image, said sequencer executes a rapid imaging sequence, and also reduces the number of phase encoding in measurement by measuring data in one part of a k space and reusing the data measured in an other part of the k space, and the apparatus further comprises image renewal means for renewing the cross-section to be imaged based on positional information of any desired angle and direction.

8. A magnetic resonance imaging apparatus according to claim 7, wherein an insertion device to be inserted to the interior of the object is provided, and said image renewal means renews the cross-section to be imaged based on positional information obtained from a portion of said insertion device which is outside of the object.

9. A magnetic resonance imaging apparatus according to claim 8, wherein said image renewal means renews the cross-section to be imaged based on the signal acquired by plural cameras for tracking movement of plural markers provided on said insertion device.

10. A magnetic resonance imaging apparatus according to claim 7, wherein said image renewal means renews a cross-section to be imaged based on positional information being signals from a three-dimensional mouse.

11. A magnetic resonance imaging apparatus according to claim 7, wherein said magnetic circuit is constituted of magnets facing each other and placed above and below the laid object, and supporting means for supporting the magnets, in which the number of supporting means is two or less.

12. A magnetic resonance imaging apparatus according to claim 7, wherein said sequencer reduces the number of phase encoding in measurement to the number of coils in said recognition system.

13. A magnetic resonance imaging apparatus according to claim 7, wherein said control means performs imaging processing for plural cross-sections to be imaged during one time period of imaging processing, and displays images of plural cross-sections during one time period of display processing.

14. A magnetic resonance imaging apparatus according to claim 13, wherein said control means determines the cross-section to be imaged obtained based on the position information brought by said image renewal means as a first imaged cross-section, and another imaged cross-section is set to be parallel to the first imaged cross-section.

15. A magnetic resonance imaging apparatus according to claim 13, wherein said control means determines the cross-section to be imaged obtained based on the positional information brought by said image renewal means as a first imaged cross-section, and the other imaged cross-sections to be perpendicular is set to the first imaged cross-section.

* * * * *